(12) United States Patent
Zorn et al.

(10) Patent No.: US 7,262,023 B2
(45) Date of Patent: Aug. 28, 2007

(54) MICROBIOLOGICAL PROCESS FOR THE PRODUCTION OF 7-SUBSTITUTED 11-HYDROXY STEROIDS, 7,17-SUBSTITUTED 11-HALOGEN STEROIDS AND USES THEREOF

(75) Inventors: Ludwig Zorn, Berlin (DE); Rolf Bohlmann, Berlin (DE); Norbert Gallus, Berlin (DE); Hermann Kuenzer, Berlin (DE); Hans-Peter Muhn, Berlin (DE); Reinhard Nubbemeyer, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 434 days.

(21) Appl. No.: 10/625,559

(22) Filed: Jul. 24, 2003

(65) Prior Publication Data

US 2005/0090477 A1   Apr. 28, 2005

Related U.S. Application Data

(60) Provisional application No. 60/402,953, filed on Aug. 14, 2002.

(30) Foreign Application Priority Data

Jul. 24, 2002   (DE) .................................. 10233723

(51) Int. Cl.
*C12P 33/10* (2006.01)
(52) U.S. Cl. ...................................................... 435/60
(58) Field of Classification Search ................. 435/55, 435/60, 52, 252.1, 254.1
See application file for complete search history.

(56) References Cited

U.S. PATENT DOCUMENTS

| | | | | | |
|---|---|---|---|---|---|
| 2,985,563 | A | * | 5/1961 | Fernando | 435/60 |
| 3,341,557 | A | * | 9/1967 | Babcock et al. | 552/647 |
| 4,557,867 | A | * | 12/1985 | Campbell | 540/30 |

FOREIGN PATENT DOCUMENTS

| WO | WO97/21830 | 6/1997 |
|---|---|---|
| WO | WO99/13812 | 3/1999 |
| WO | WO 02/059139 | 8/2002 |
| WO | WO 2004/011008 | 2/2004 |

OTHER PUBLICATIONS

Tan L et al., "Interactions of Steroids and Fungi. 11 Alpha-hydroxylation and Degradation. of Progestrone-4-C by a Cell-free Preparation from Aspergillus Ochraceus," Journal of Steroid Biochemistry, Sep. 1, 1970, pp. 221-227, vol. 1, No. 3, XP000671122, ISSN: 0022-4731, the entire document, Pergamon Press PLC, GB.
Shibahara M et al., "Microbial Hydroxylations V. lialpha-hyroxylation of Progestrone by cell-free preparations of Aspergillus Ochraceus," Biochimica Et Biophysica Acta, 1970, pp. 172-179, vol. 202, XP009023368, ISSN: 0006-3002, the entire document, Amsterdam, NL.

* cited by examiner

*Primary Examiner*—Leon B. Lankford, Jr.
*Assistant Examiner*—Susan Hanley
(74) *Attorney, Agent, or Firm*—Millen, White, Zelano, Branigan, P.C.

(57) ABSTRACT

A novel method of synthesis for the manufacture of upstream products for the production of compounds with general formulas 8, 10, and 12 is described. In this synthesis, compounds with general formula 4,B are produced in a microbiological reaction. The meanings of $R^7$, $R^{10}$, $R^{11}$, $R^{13}$, $R^{17}$ and $R^{17'}$ as well as of the grouping U—V—W—X—Y—Z are indicated in the claims

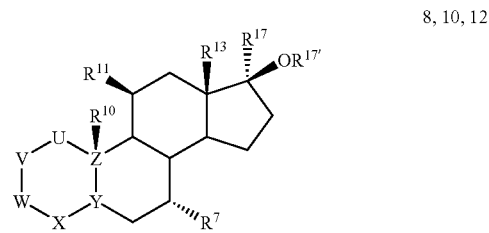

8, 10, 12

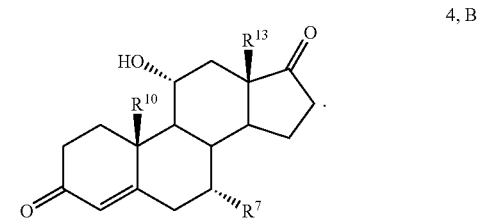

4, B

10 Claims, No Drawings

MICROBIOLOGICAL PROCESS FOR THE PRODUCTION OF 7-SUBSTITUTED 11-HYDROXY STEROIDS, 7,17-SUBSTITUTED 11-HALOGEN STEROIDS AND USES THEREOF

This application claims the benefit of the filing date of U.S. Provisional Application Ser. No. 60/402,953 filed Aug. 14, 2002.

DESCRIPTION

The invention relates to microbiological processes for the production of 7α-substituted 11α-hydroxy steroids, 7α,17α-substituted 11β-halogen steroids that can be produced therefrom, production processes for the latter compounds as well as their use and pharmaceutical preparations that contain these compounds. In addition, the invention relates to other 7α-substituted 11β-halogen steroids, namely 7α-substituted estra-1,3,5(10)-trienes that can be obtained from the 7α-substituted 11α-hydroxy steroids.

For treatment of male menopause and for development of male sexual organs as well as for male birth control, androgens, especially testosterone, are used. In addition, these hormones also have partial anabolic active components, which promote, i.a., muscle growth.

Male menopause is characterized by an age-related reduction in the endogenous androgen production, such that hormone replacement is carried out for treatment thereof (HRT: hormone replacement therapy).

In addition to a reduction in spermatogenesis, the LH-RH administration for male birth control also results in the release of LH and in the dropping of testosterone levels and libido, which are compensated for by administering testosterone pharmaceutical agents (D. E. Cummings et al., "Prostate-Sparing Effects of the Potent Androgen 7α-Methyl-19-Nortestosterone: A Potential Alternative to Testosterone for Androgen Replacement and Male Contraception," Journal of Clinical Endocrinology and Metabolism, Vol. 83, No. 12, pages 4212-4219 (1998)).

A combination therapy with the administration of androgens and a gestagenically active component can be used for control of male fertility (see, for example, WO 01/60376 A as well as the documents cited therein).

In the case of a treatment with testosterone, it has been shown that side effects develop, especially an enlargement of the prostate owing to an increase in the number of cells and glands of the stroma (BPH: benign prostate hyperplasia). In the metabolism of testosterone that is mediated by 5α-reductase, dihydrotestosterone (DHT) that can result, i.a., in the occurrence of BPH is produced (Cummings et al., ibid.; WO 99/13883 A1). The inhibition of the 5α-reductase is therefore used for treating BPH in clinical practice (finasterides).

The quick metabolism of the androgenic steroid testosterone in the human body further results not only in the formation of undesirable DHT, but also in that an oral administration of higher doses is necessary to reach the desired effect level of testosterone. Alternative forms for dispensing, such as i.m.-injections or large patches, are therefore necessary.

To replace testosterone in the above-mentioned indication areas, 7α-methyl-19-nortestosterone (MeNT) was proposed which has, on the one hand, a higher biological effectiveness as testosterone, since it has a higher binding affinity to the androgen receptors. On the other hand, because of a steric inhibition by the 7α-methyl group, it presumably resists metabolization by 5α-reductase (Cummings et al., ibid., WO 99/13883 A1, WO 99/13812 A1, U.S. Pat. No. 5,342,834).

During metabolism of testosterone, a smaller portion of this compound is also reacted by aromatization of ring A of the steroid system to form estradiol, especially in the brain, in the liver and in the fatty tissue. With respect to the total action of the testosterone and its metabolites, estradiol is substantially responsible for sex-specific behavior and gonadotrophin regulation. Therefore, its action just like that of testosterone for the adult male is regarded as advantageous (Cummings et al., ibid.).

It has been shown, however, that the pharmacokinetics of testosterone is not satisfactory. In particular in the case of oral dispensing, testosterone is quickly excreted again, so that the effectiveness and the duration of action of the thus produced pharmaceutical agents is unsatisfactory. Other testosterone derivatives were therefore also synthesized. Such derivatives are described in, i.a., U.S. Pat. No. 5,952,319, in particular 7α-,11β-dimethyl derivatives of 19-nortestosterone, namely 7α, 11β-dimethyl-17β-hydroxyestr-4-en-3-one, 7α, 11β-dimethyl-17β-heptanoyloxyestr-4-en-3-one, 7α, 11β-dimethyl-17β-[[(2-cyclopentylethyl)-carbonyl]-oxy]-estr-4-en-3-one, 7α, 11β-dimethyl-17β-(phenylacetyloxy)-estr-4-en-3-one, and 7α, 11β-dimethyl-17β-[[(trans-4-[n-butyl]cyclohexyl)-carbonyl]-oxy]-estr-4-en-3-one.

The above-mentioned 7α, 11β-dimethyl derivatives have the above-mentioned advantages, like MeNT, including an improved pharmacokinetics, i.e., their effectiveness and duration of action are improved relative to testosterone. These derivatives, however, can be produced only via an expensive synthesis method.

A synthesis of steroids in the microbiological method is described in EP 0 900 283 B1. It is indicated there that estr-4-ene-3,17-dione and canrenone can be transformed with use of a microorganism that is selected from the group that comprises Apergillus nigricans, Rhizopus arrhizus and strains of Pestelotia into the corresponding 11α-hydroxy analog. In the introduction of the description, however, reference is also made to Shibahara et al., Biochim. Biophys. Acta, 202 (1970), 172-179, who reported that the microbiological 11α-hydroxylation reaction in steroids can be unpredictable.

The problem on which this invention is based is therefore to find derivatives of testosterone that are not sensitive relative to a reduction by means of 5α-reductase, that also have an improved pharmacokinetics, and that are especially easy to produce. A very significant aspect of this invention consequently consists in finding a process for better accessibility of the initial products, with which the initial products are easy to produce.

The problem on which this invention is based is solved by microbiological processes for the production of 7α-substituted steroids as follows:

microbiological process for the production of 7α-substituted 11α-hydroxy steroids with general formula 4,B:

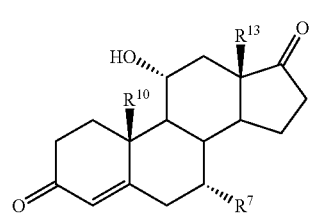

in which
R[7] is the grouping P-Q, whereby
  P represents a $C_1$- to $C_4$-alkylene, and Q represents a $C_1$- to $C_4$-alkyl- or $C_1$- to $C_4$-fluoroalkyl, and the grouping P-Q is bonded via P to the steroid skeleton,
R[10] can be in α- or β-position and stands for H, $CH_3$ or $CF_3$, and
R[13] is methyl or ethyl, in which a 7α-substituted steroid with general formula 3,A:

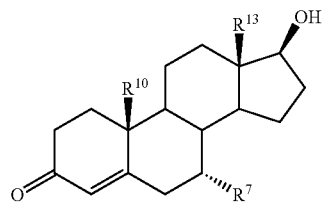

3,A in which R[7,] R[10] and R[13] have the same meanings as indicated above, is hydroxylated and oxidized with use of a microorganism that is selected from the group that comprises *Aspergillus sp., Beauveria sp., Glomerella sp., Gnomonia., Haplosporella sp.* and *Rhizopus sp;*
  microbiological process for the production of 7α-substituted 11α-hydroxy steroids with general formula 4,B:

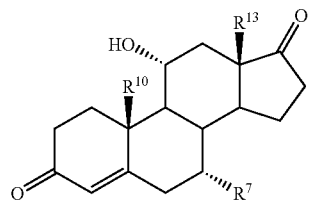

4,B in which
R[7] is the grouping P-Q, whereby
  P represents a $C_1$- to $C_4$-alkylene and Q represents a $C_1$- to $C_4$-alkyl- or $C_1$- to $C_4$-fluoroalkyl, and the grouping P-Q is bonded via P to the steroid skeleton,
R[10] can be in α- or β-position and stands for H, $CH_3$ or $CF_3$, and
R[13] is methyl or ethyl, in which a 7α-substituted steroid with general formula 3,A:

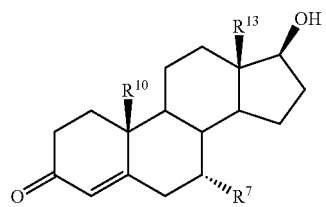

3,A in which R[7,] R[10] and R[13] have the same meanings as previously indicated, is hydroxylated in 11α-position in a first microbiological process step with use of a first microorganism that is selected from the group that comprises *Aspergillus sp., Beauveria sp., Gibberella sp., Glomerella sp., Gnomonia sp., Metarrhizium sp., Nigrospora sp., Rhizopus sp.* and *Verticillium sp.*, with the formation of a 7α-substituted 11β-hydroxy steroid with general formula C:

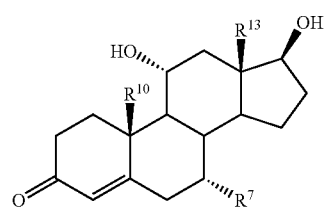

C in which R[7,] R[10] and R[13] have the same meanings as indicated above, and
  the 7α-substituted 11α-hydroxy steroid with general formula C that is produced is then oxidized in a second microbiological process step with use of a second microorganism that is selected from the group that comprises *Bacillus sp., Mycobacterium sp., Nocardia sp.* and *Pseudomonas sp.*, with the formation of the 7α-substituted steroid with general formula 4,B;
  microbiological process for the production of 7α-substituted 11α-hydroxy steroids with general formula 4,B:

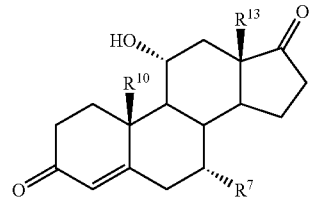

4,B in which
R[7] is the grouping P-Q, whereby
  P represents a $C_1$- to $C_4$-alkylene and Q represents a $C_1$- to $C_4$-alkyl- or $C_1$- to $C_4$-fluoroalkyl, and the grouping P-Q is bonded via P to the steroid skeleton,
R[10] stands for H, $CH_3$ or $CF_3$, and
R[13] is methyl or ethyl, in which 7α-substituted steroids with general formula D:

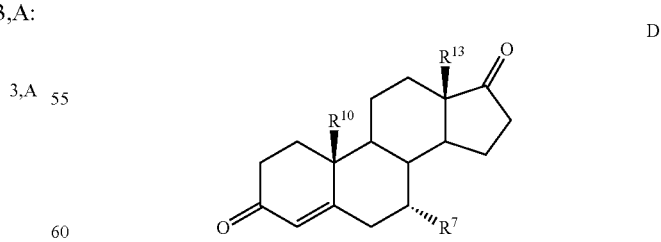

D in which R[7,] R[10] and R[13] have the same meanings as indicated above,
  are hydroxylated with use of a microorganism that is selected from the group that comprises *Aspergillus sp., Beauveria sp., Curvularia sp., Gibberella sp., Glomer-* ella sp., Gnomonia sp., Haplosporella sp., Helicostylum sp., Nigrospora sp., Rhizopus sp. and Syncephalastrum sp;

7α, 17α-Substituted 11β-halogen steroids with general formulas 8, 10, and 12:

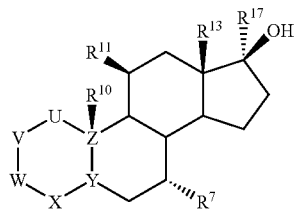

8,10,12 in which
U-V-W-X-Y-Z stands for one of ring structures $C^1$-$C^2$-$C^3$-$C^4$=$C^5$-$C^{10}$, $C^1$-$C^2$-$C^3$-$C^4$-$C^5$=$C^{10}$ or $C^1$-$C^2$-$C^3$-$C^4$-$C^5$-$C^{10}$, whereby in this case, an oxo group (=O) is bonded to W (=C), or for ring structure $C^1$=$C^2$-$C^3$=$C^4$-$C^5$=$C^6$, whereby in this case radical $OR^3$ is bonded to W (=$C^3$),
$R^3$ stands for H, $C_1$- to $C_4$-alkyl, $C_1$- to $C_4$-alkanoyl or a cyclic $C_3$- to $C_7$-ether
with
the O-atom of the $OR^3$-radical,
$R^7$ is the grouping P-Q, whereby
P represents a $C_1$- to $C_4$-alkylene and Q represents a $C_1$- to $C_4$-alkyl- or $C_1$- to $C_4$-fluoroalkyl, and grouping P-Q is bonded via P to the steroid skeleton,
$R^{10}$ can be in α- or β-position and stands for H, $CH_3$ or $CF_3$, and is present only
if
X-Y-Z is not $C^4$-$C^5$=$C^{10}$,
$R^{11}$ is a halogen,
$R^{13}$ is methyl or ethyl,
$R^{17}$ stands for H, $C_1$- to $C_{18}$-alkyl, alicyclic $C_1$- to $C_{18}$-alkyl, $C_1$- to $C_{18}$-alkenyl, alicyclic $C_1$- to $C_{18}$-alkenyl, $C_1$- to $C_{18}$-alkylaryl, $C_1$- to $C_8$-alkylenenitrile or for the grouping P-Q, whereby the grouping P-Q has the above-mentioned meaning,
$R^{17'}$ stands for H, $C_1$- to $C_{18}$-alkyl, alicyclic $C_1$- to $C_{18}$-alkyl, $C_1$- to $C_{18}$-alkenyl,
alicyclic $C_1$- to $C_{18}$-alkenyl, $C_1$- to $C_{18}$-alkinyl or $C_1$- to $C_{18}$-alkylaryl, whereby $R^{17'}$ also can be bonded via a keto group to the 17β-oxy group, and whereby $R^{17'}$ also in addition can be substituted with one or more groups $NR^{18}R^{19}$ or one or more groups $SO_xR^{20}$, whereby x =0, 1 or 2 and $R^{18}$, $R^{19}$ and $R^{20}$ in each case independently of one another can have the same meaning as $R^{17}$, as well as their pharmaceutically compatible addition salts, esters and amides; process for the production of 7α, 17α-substituted 11β-halogen steroids as follows:

process for the production of 7α, 17β-substituted 11β-halogen steroids with general formula 10 in which U-V-W-X-Y-Z stands for the ring structure $C^1$-$C^2$-$C^3$-$C^4$=$C^5$-$C^{10}$, with the following process steps:
Nucleophilic substitution in a 7α-substituted 11α-hydroxy steroid with general formula 4,B in 11-position with a halodehydroxylating reagent;
Reaction of the 7α-substituted 11β-halogen steroid that is produced in this case with an alkylating agent in a selective manner on the $C^{17}$ atom of the ring skeleton to form the 7α, 17β-substituted 11β-halogen steroid with general formula 10; process for the production of 7α, 17α-substituted 11β-halogen steroids with general formula 12 in which U-V-W-X-Y-Z stands for the ring structure $C^1$-$C^2$-$C^3$-$C^4$-$C^5$=$C^{10}$, with the following process steps:
Nucleophilic substitution in a 7α-substituted 11α-hydroxy steroid with general formula 4,B in 11-position with a halodehydroxylating reagent,
Reaction of the 7α-substituted 11β-halogen steroid that is produced in this case with an alkylating agent in a selective manner on the $C^{17}$ atom of the ring skeleton to form the 7α, 17α-substituted 11β-halogen steroid with general formula 10,
Isomerization of the 7α, 17α-substituted 11β-halogen steroid with general formula 10 to form the corresponding isomer with general formula 12, in which U-V-W-X-Y-Z stands for the ring structure $C^1$-$C^2$-$C^3$ $C^4$ -$C^5$ =$C^{10}$; process for the production of 7α, 17α-substituted 11β-halogen steroids with general formula 8 in which U-V-W-X-Y-Z stands for the ring structure $C^1$=$C^2$-$C^3$=$C^4$-$C^5$=$C^6$ with the following process steps:
Nucleophilic substitution in a 7α-substituted 11α-hydroxy steroid with general formula 4,B in 11-position with a halodehydroxylating reagent,
Oxidizing of the 7α-substituted 11 13-halogen steroid that is produced in this case to form 7α-substituted estra-1,3,5 (10)-triene with general formula 6;
Reaction of the 7α-substituted estra-1,3,5(10)-triene with general formula 6 with an alkylating agent in a selective manner on the $C^{17}$ atom of the ring skeleton to form the 7α, 17α-substituted 11β-halogen steroid with general formula 8; use of the 7α, 17α-substituted 11β-halogen steroids with general formulas 8, 10, and 12 for the production of pharmaceutical agents;
pharmaceutical preparations that contain at least one 7α, 17α-substituted 11β-halogen steroid with general formulas 8,10, and 12 as well as at least one pharmaceutically compatible vehicle; as well as 7α-Substituted 11βhaloestra-1,3,5(10)trienes with general formula 6:

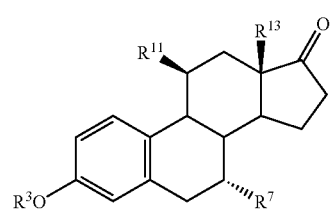

6 in which
$R^3$ stands for H, $C_1$- to $C_4$-alkyl, $C_1$- to $C_4$-alkanoyl or a cyclic $C_3$- to $C_7$-ether with the O-atom of the $OR^3$-radical,
$R^7$ is the grouping P-Q, whereby
P represents a $C_1$- to $C_4$-alkylene and Q represents a $C_1$- to $C_4$-alkyl- or $C_1$- to $C_4$-fluoroalkyl, and the grouping P-Q is bonded via P to the steroid skeleton,
$R^{11}$ is a halogen;
$R^{13}$ is methyl or ethyl, as well as their pharmaceutically compatible addition salts, esters and amides.

Definitions:
The definitions below relate to all portions of the description and the claims as well as to Diagram I that is attached:

All groupings, radicals or other structural units can in each case be varied independently of one another within the indicated areas of meaning.

All alkyl, alkylene, alkenyl, alkenylene, alkinyl, and alkinylene groups can be either straight-chain or branched. For example, a propenyl group can be described by one of the chemical structures below: —CH=C—CH$_3$, —CH$_2$—C=CH$_2$, or —C(CH$_3$)=CH$_2$. Thus, for example, methyl, ethyl, n-propyl, i-propyl, n-butyl, i-butyl, t-butyl, n-pentyl, i-pentyl, t-pentyl, neo-pentyl, n-hexyl, 1-methyl-n-pentyl, 2-methyl-n-pentyl, 3-methyl-n-pentyl, 4-methyl-n-pentyl, 1-ethyl-n-butyl, 2-ethyl-n-butyl, etc., fall under C$_1$— to C$_{18}$-alkyl.

Alicyclic alkyl is either a cycloalkyl or a cycloalkyl that is substituted with one alkyl group or several alkyl groups, which is bonded directly via the cycloalkyl ring or via one of the alkyl groups.

In the same way, an alicyclic alkenyl is either a cycloalkenyl or a cycloalkenyl or cycloalkyl that is substituted with one or more alkenyl groups or with one or more alkenyl groups and alkyl groups or with one or more alkyl groups, which is bonded directly via the cycloalkenyl ring or via one of the alkenyl groups or optionally alkyl groups, whereby at least one double bond is contained in the alicyclic alkenyl.

On the one hand, aryl can be phenyl, but also 1-naphthyl or 2-naphthyl. In principle, aryl also includes heteroaryl, especially 2-, 3- and 4-pyridinyl, 2- and 3-furyl-, 2- and 3-thienyl, 2- and 3-pyrrolyl, 2-, 4- and 5-imidazolyl, pyridazinyl, 2-, 4- and 5-pyrimidinyl as well as 3- and 4-pyridazinyl.

Halogen is fluorine, chlorine, bromine or iodine.

Pharmaceutically compatible addition salts are salts of the corresponding compounds with inorganic or organic acids, for example with hydrochloric acid, hydrobromic acid, hydroiodic acid, acetic acid, citric acid, oxalic acid, tartaric acid and methanesulfonic acid. The esters can be formed in particular with succinic acid.

Superscript numbers on symbols R, for example R$^{13}$, designate their position on the steroid ring skeleton, whereby the C atoms in the steroid ring skeleton are numbered according to IUPAC nomenclature. Superscript numbers on symbols C, for example C$^{10}$, designate the position of the respective carbon atom in the steroid ring skeleton.

DESCRIPTION OF THE INVENTION

Novel microbiological processes are used for the production of 7α-substituted 11α-hydroxy steroids with general formula 4,B:

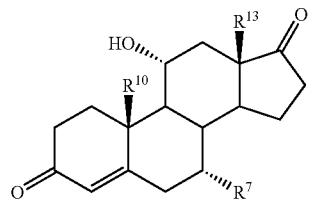

4,B in which
R$^7$ is the grouping P—Q, whereby P represents C$_1$- to C$_4$-alkylene and Q represents a C$_1$- to C$_4$-alkyl- or C$_1$— to C$_4$-fluoroalkyl (alkyl that is partially or completely fluorinated), and grouping P—Q is bonded via P to the steroid skeleton, R$^{10}$ stands for H, CH$_3$ or CF$_3$, and
R$^{13}$ is methyl or ethyl.

In a first process variant for the production of these substances, a suitable 7α-substituted steroid with general formula 3,A:

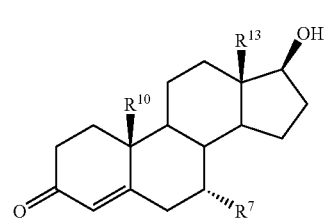

3,A in which R$^7$, R$^{10}$ and R$^{13}$ have the same meanings as indicated for the compounds with general formula 4,B, is hydroxylated and oxidized in one process step with use of a microorganism that is selected from the group that comprises *Aspergillus* sp., *Beauveria* sp., *Glomerella* sp., *Gnomonia* sp., *Haplosporella* sp. and *Rhizopus* sp. Especially preferred are *Aspergillus awamori*, *Aspergillus fischeri*, *Aspergillus malignus*, *Aspergillus niger*, *Beauveria bassiana*, *Glomerella cingulata*, *Gnomonia cingulata*, *Haplosporella hesperedica* and *Rhizopus stolonifer*, whereby in particular *Aspergillus awamori* (CBS), *Aspergillus fischeri* (ATCC 1020), *Aspergillus malignus* (IMI 16061), *Aspergillus niger* (ATCC 9142), *Beauveria bassiana* (ATCC 7159), *Glomerella cingulata* (CBS 15226, CBS 23849, CBS 98069, ATCC 56596, ATCC 64682, IFO 6425), *Gnomonia cingulata* (CBS 15226), *Haplosporella hesperedica* (CBS 20837) and *Rhizopus stolonifer* (ATCC 15441) are used.

As an alternative, this microbiolgoical production process can also be performed in two stages, whereby the hydroxylation reaction and the oxidation reaction take place in sequential reaction steps. The course of the reaction can be controlled via the reaction period: by the reaction being interrupted, for example, after a certain reaction time, the hydroxylated, but still not oxidized species can be isolated. Both process steps can therefore be performed separately or in a mixed fermentation.

To this end, the compound can be hydroxylated in 11-position with general formula 3,A in a first microbiological process step with use of a first microorganism, selected from the group that comprises *Aspergillus* sp., *Beauveria* sp., *Gibberella* sp., *Glomerella* sp., *Gnomonia* sp., *Metarrhizium* sp., *Nigrospora* sp., *Rhizopus* sp. and *Verticillium* sp., whereby a 7α-substituted steroid is formed with a hydroxy group in 11α-position. This compound has general formula C:

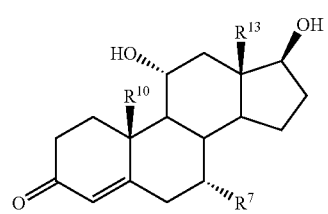

C in which R$^7$, R$^{10}$ and R$^{13}$ have the same meanings as indicated above for the compounds with general formula 4,B. Used in particular are *Aspergillus malignus, Aspergillus melleus, Aspergillus niger, Aspergillus ochraceus, Beauveria bassiana, Gibberella fujikuroi, Gibberella zeae, Glomerella cingulata, Glomerella fusaroides, Gnomonia cingulata, Metarrhizium anisopliae, Nigrospora sphaerica, Rhizopus oryzae, Rhizopus stolonifer* and *Verticillium dahliae*. In this connection, especially *Aspergillus malignus* (IMI 16061), *Aspergillus melleus* (CBS), *Aspergillus niger* (ATCC 11394), *Aspergillus ochraceus* (NRRL 405, CBS 13252, ATCC 46504), *Beauveria bassiana* (ATCC 7159, IFO 5838, ATCC 13144, IFO 4848, CBS 11025, CBS 12736), *Gibberella fujikuroi* (ATCC 14842), *Gibberella zeae* (CBS 4474), *Glomerella cingulata* (ATCC 10534, CBS 23849, CBS 23749, ATCC 16646, ATCC 16052, IFO 6459, IFO 6425, IFO 6470, CBS 98069, IFO 7478, IFO 5257, ATCC 64682, ATCC 15470), *Glomerella fusaroides* (ATCC 9552), *Gnomonia cingulata* (CBS 15226), *Metarrhizium anisopliae* (IFO 5940), *Nigrospora sphaerica* (ATCC 12772), *Rhizopus oryzae* (ATCC 4858, ATCC 34102, ATCC 34102), *Rhizopus stolonifer* (ATCC 6227b, ATCC 15441) and *Verticillium dahliae* (ATCC 11405) are used for the hydroxylation.

Intermediate product C is then oxidized in a second microbiological process step with use of a second microorganism that is selected from the group that comprises *Bacillus* sp., *Mycobacterium* sp., *Nocardia* sp. and *Pseudomonas* sp., with the formation of 7α-substituted 11α-hydroxy steroids with general formula 4,B. Used in particular are *Bacillus lactimorbus, Bacillus sphaericus, Mycobacterium neoaurum, Mycobacterium smegmatis, Nocardia corallina, Nocardia globerula, Nocardia minima, Nocardia restrictus, Nocardia rubropertincta, Nocardia salmonicolor* and *Pseudomonas testosteroni*, whereby in particular *Bacillus lactimorbus* (ATCC 245), *Bacillus sphaericus* (ATCC 7055), *Mycobacterium neoaurum* (ATCC 9626, NRRL B-3683, NRRL B-3805), *Mycobacterium smegmatis* (ATCC 14468), *Nocardia corallina* (ATCC 31338) *Nocardia globerula* (ATCC 9356), *Nocardia minima* (ATCC 19150), *Nocardia restrictus* (NCIB 10027), *Nocardia rubropertincta* (ATCC 14352), *Nocardia salmonicolor* (ATCC 19149) and *Pseudomonas testosteroni* (ATCC 11996) are used.

In another process variant, the compounds with general formula 4,B can be produced in a microbiological reaction from 7α-substituted steroids with general formula D:

D in which $R^7$, $R^{10}$ and $R^{13}$ have the same meanings as indicated in the compounds with general formula 4,B. This reaction is performed with use of a microorganism that is selected from the group that comprises *Aspergillus* sp., *Beauveria* sp., *Curvularia* sp., *Gibberella* sp., *Glomerella* sp., *Gnomonia* sp., *Haplosporella* sp., *Helicostylum* sp., *Nigrospora* sp., *Rhizopus* sp. and *Syncephalastrum* sp., whereby the steroid skeleton is hydroxylated in 11α-position and thus the 7α-substituted 11α-hydroxy steroid with general formula 4,B is produced. *Aspergillus alliaceus, Aspergillus awamori, Aspergillus fischeri, Aspergillus malignus, Aspergillus melleus, Aspergillus nidualans, Aspergillus niger, Aspergillus ochraceus, Aspergillus variecolor, Beauveria bassiana, Curvularia lunata, Gibberella zeae, Glomerella cingulata, Glomerella fusaroides, Gnomonia cingulata, Haplosporella hesperedica, Helicostylum piriformae, Nigrospora sphaerica, Rhizopus oryzae* and *Syncephalastrum racemosum* are preferred, whereby in particular *Aspergillus alliaceus* (ATCC 10060), *Aspergillus awamori* (CBS), *Aspergillus fischeri* (ATCC 1020), *Aspergillus malignus* (IMI 16061), *Aspergillus melleus* (CBS), *Aspergillus nidualans* (ATCC 11267), *Aspergillus niger* (ATCC 9142, ATCC 11394), *Aspergillus ochraceus* (NRRL 405, ATCC 13252, ATCC 46504), *Aspergillus variecolor* (ATCC 10067), *Beauveria bassiana* (IFO 5838, ATCC 13144, IFO 4848, CBS 11025, CBS 12736, ATCC 7159), *Curvularia lunata* (IX3), *Gibberella zeae* (CBS 4474), *Glomerella cingulata* (ATCC 10534, CBS 23849, CBS 23749, ATCC 16646, IFO 6459, IFO 6425, IFO, 6470, ATCC 15093, ATCC 10529, IFO 5257, ATCC 56596, ATCC 64682), *Glomerella fusaroides* (ATCC 9552), *Gnomonia cingulata* (CBS 15226), *Haplosporella hesperedica* (CBS 20837), *Helicostylum piriformae* (ATCC 8992), *Nigrospora sphaerica* (ATCC 12772), *Rhizopus oryzae* (ATCC 4858) and *Syncephalastrum racemosum* (IFO 4827) are used.

Especially suitable are processes in which 7α-substituted 11 α-hydroxy steroids with general formula 4,B are produced, in which, independently of one another, $R^7$ stands for $CH_3$ and/or $R^{10}$ stands for H and/or $R^{13}$ stands for $CH_3$.

The process is carried out in the usual way. To this end, typically first a sterilized nutrient solution is produced for the strain, and this nutrient solution is then inoculated with the culture solution of the strain to cultivate the strain. The preculture that is produced in this way is then added to a fermenter that is optionally coated with a suitable nutrient solution. Preferably after a growth phase for the culture of the strain, the starting substance is then added to the fermenter, in this case either a compound with general formula 3,A or a compound with general formula D, so that the reaction according to the invention can proceed. After the reaction has ended, the mixture of substances is purified in the usual way to isolate the desired 7α-substituted 11α-hydroxy steroid.

From the thus obtained compounds with general formula 4,B, other compounds according to the invention can be synthesized with production processes also according to the invention. In particular, the 7α, 17α-substituted 11β-halogen steroids with general formula 8, 10, and 12:

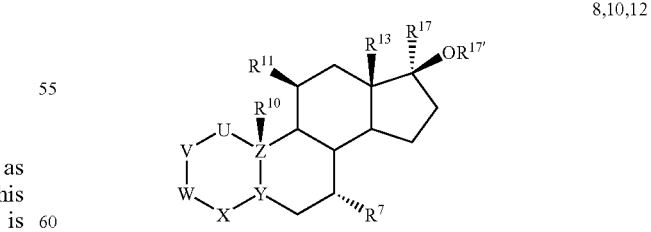

8,10,12 in which

U—V—W—X—Y—Z stands for one of the ring structures $C^1—C^2—C^3—C^4=C^5—C^{10}$, $C^1—C^2—C^3—C^4—C^5=C^{10}$ or $C^1—C^2—C^3—C^4—C^5—C^{10}$, whereby in this case, an oxo group (=O) is bonded to W (=C³), or for the ring structure C¹=C²—C³=C⁴—C⁵=C⁶, whereby in this case radical OR³ is bonded to W (=C³), $R^3$ stands for H, $C_1$- to $C_4$-alkyl, $C_1$- to $C_4$-alkanoyl or a cyclic $C_3$- to $C_7$-ether with the O-atom of the OR³ radical, $R^7$ is the grouping P—Q, whereby P represents a $C_1$- to $C_4$-alkylene and Q represents a $C_1$- to $C_4$-alkyl- or $C_1$- to $C_4$-fluoroalkyl (alkyl that is partially or completely fluorinated), and the grouping P—Q is bonded via P to the steroid skeleton, $R^{10}$ can be in α- or β-position and stands for H, $CH_3$ or $CF_3$, and is present only if X—Y—Z is not C⁴—C⁵=C¹⁰, $R^{11}$ is a halogen, $R^{13}$ is methyl or ethyl, $R^{17}$ stands for H, $C_1$- to $C_{18}$-alkyl, alicyclic $C_1$- to $C_{18}$-alkyl, $C_1$- to $C_{18}$-alkenyl, alicyclic $C_1$- to $C_{18}$-alkenyl, $C_1$- to $C_{18}$-alkinyl, $C_1$- to $C_{18}$-alkylaryl, $C_1$- to $C_8$-alkylenenitrile or for the grouping P—Q, whereby the grouping P—Q has the above-mentioned meaning, $R^{17'}$ stands for H, $C_1$- to $C_{18}$-alkyl, alicyclic $C_1$- to $C_{18}$-alkyl, $C_1$- to $C_{18}$-alkenyl, alicyclic $C_1$- to $C_{18}$-alkenyl, $C_1$- to $C_{18}$-alkinyl or $C_1$- to $C_{18}$-alkylaryl, whereby $R^{17'}$ also can be bonded via a keto group to the 17β-oxy group, and whereby $R^{17'}$ also can be substituted in addition with one or more groups $NR^{18}R^{19}$ or one or more groups $SO_xR^{20}$, whereby x=0, 1 or 2, and $R^{18}$, $R^{19}$ and $R^{20}$ in each case independently of one another can have the same meaning as $R^{17}$, as well as their pharmaceutically compatible addition salts, esters and amides, produce advantageous active ingredients. These compounds that can be obtained by additional process steps from the 7α-substituted 11α-hydroxy steroid with general formula 4,B are valuable active ingredients with strong androgenic action without the above-mentioned side effects. These compounds are suitable for the production of pharmaceutical agents and especially of effective contraceptive agents and active ingredients for hormone replacement therapy (HRT).

If, in addition, $R^{17'}$ is substituted with a group $NR^{18}R^{19}$, this can be a methylamino, dimethylamino, ethylamino, diethylamino, cyclohexylamino, dicyclohexylamino, phenylamino, diphenylamino, benzylamino or dibenzylamino group.

Especially suitable 7α, 17α-substituted 11β-halogen steroids with general formulas 8, 10, and 12 are compounds in which U—V—W—X—Y—Z stands for the ring structure C¹—C²—C³—C⁴=C⁵—C¹⁰, C¹—C²—C³—C⁴—C⁵=C¹⁰ or C¹=C²—C³=C⁴—C⁵=C¹⁰.

In the first case, (U—V—W—X—Y—Z=C¹—C²—C³—C⁴=C⁵—C¹⁰), these are steroids with general formula 10:

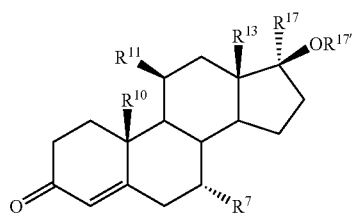

10

In the second case (U—V—W—X—Y—Z=C¹—C²—C³—C⁴—C⁵=C¹⁰), these are steroids with general formula 12:

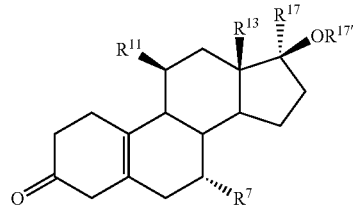

12

Compounds with general formulas 10 and 12 are androgenic compounds.

In the third case (U—V—W—X—Y—Z=C1=C2-C3=C4-C5=C6), these are steroids with general formula 8:

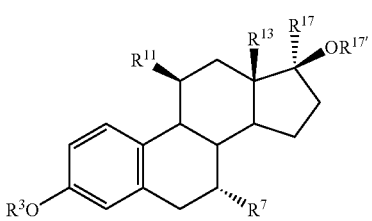

8

These compounds are estrogens (estrogen rezeptor-affine compounds).

In all three cases, radicals $R^3$, $R^7$, $R^{10}$, $R^{11}$, $R^{13}$, $R^{17}$ and $R^{17'}$ have the same meanings as the corresponding radicals in general formulas 8, 10, and 12.

Independently of one another, $R^1$ preferably stands for H and/or $R^7$ stands for $CH_3$ and/or $R^{11}$ stands for fluorine and/or $R^{13}$ stands for $CH_3$ and/or $R^{17}$ stands for H, $CH_3$, $C_1$— to $C_{18}$-alkinyl, in particular ethinyl, $CH_2CN$ or $CF_3$ and/or $R^{17'}$ stands for H.

7α, 17α-Substituted 11β-halogen steroids with general formulas 8, 10, and 12 that are especially suitable according to the invention are:

17α-Ethinyl-11β-fluoro-17β-hydroxy-7α-methylestr-4-en-3-one (Formula 10)

17α-Ethinyl-11β-fluoro-17β-hydroxy-7α-methylestr-5(10)-en-3-one (Formula 12)

17α-Ethinyl-11β-fluoro-7α-methylestra-1,3,5(10)-triene-3,17β-diol (Formula 8).

For the production of these compounds, the following production methods can be adopted:

For the production of 7α, 17α-substituted 11β-halogen steroids with general formula 10, in which U—V—W—X—Y—Z stands for the ring structure C¹—C²—C³—C⁴=C⁵—C¹⁰, the 7α-substituted 11α-hydroxy steroids with general formula 4,B that are obtained with the microbiological production process according to the invention are used as starting substances.

In a first synthesis step, these thus obtained 7α-substituted 11α-hydroxy steroids are converted by nucleophilic substitution with a halodehydroxylating reagent into the corresponding 7α-substituted 11β-halogen steroids 5:

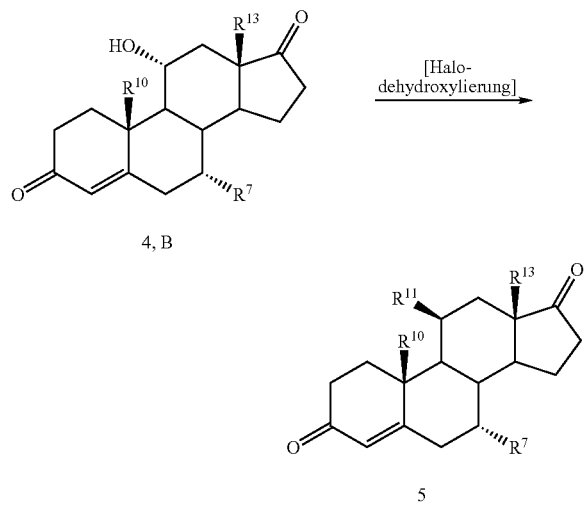

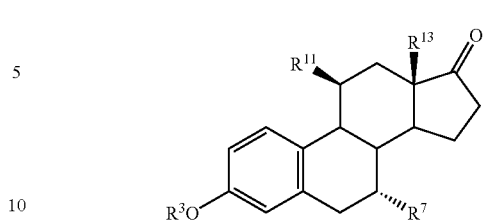

4, B

5

[Key: Halodehydroxylierung=halodehydroxylation]

As halodehydroxylating reagents, all compounds that are commonly used for this purpose are suitable, for example, hydrofluoric acid, hydrochloric acid, hydrobromic acid or hydroiodic acid, thionyl chloride or thionyl bromide, phosphorus pentachloride, phosphorus oxychloride, N-chlorosuccinimide, triphenylphosphine/carbon tetrachloride, HF/pyridine or diethylaminosulfur trifluoride or preferably nonaflyl fluoride/1,5-diazabicyclo[5.4.0]undecene.

Compound 10 is then produced from 5 by selective alkylation on $C^{17}$ of the ring skeleton (see Diagram 1 in this respect). For selective alkylation, common alkylating reagents can be used, for example Grignard compounds and organometallic compounds, especially alkyllithium compounds. For example, ethinylmagnesium bromide can be used as an alkylating agent for the production of the corresponding 17α-ethinyl-17β-hydroxy-estr-4-en-3-one from estr-4-ene-3,17-dione.

For the production of 7α, 17α-substituted 11β-halogen steroids, in which U—V—W—X—Y—Z stands for the ring structure $C^1$—$C^2$—$C^3$—$C^4$—$C^5$=$C^{10}$ and which have general formula 12, the compounds with general formula 10 are used and isomerized, such that the $\Delta^4$-double bond is isomerized into a $\Delta^{5(10)}$-double bond. To protect the 3-keto group, first a cyclic ether is formed in 3-position for this purpose. Then, the $\Delta^4$-double bond is isomerized into the $\Delta^{5(10)}$-double bond, whereby the 7α, 17α-substituted 11β-halogen steroid with general formula 12 is formed, and the protective group is cleaved again.

For the production of additional 7α, 17α-substituted 11β-halogen steroids with general formula 8, in which U—V—W—X—Y—Z stands for $C^1$=$C^2$—$C^3$=$C^4$—$C^5$=$C^{10}$, the procedure is as follows:

First, as already described above, the corresponding 11β-halogen steroid with general formula 5 is formed from the 7α-substituted 11α-hydroxy steroid, obtained by microbiological hydroxylation and oxidation, with general formula 4,B by halodehydroxylation in a nucleophilic substitution reaction.

From the latter, a 7α-substituted estra-1,3,5(10)-triene with general formula 6 is then formed by oxidation, for example with a copper(II) salt:

6 in which $R^3$, $R^7$, $R^{11}$ and $R^{13}$ have the same meanings as designated above. If $R^3$ stands for H, these compounds can be synthesized directly. If another radical is to stand as H for $R^3$, the corresponding ethers or esters must be formed in the known way, after the 1,3,5(10)-triene ring has been formed by oxidation.

The 7α-substituted 11β-haloestra-1,3,5(10)-trienes with general formula 6 as well as pharmaceutically compatible addition salts, esters and amides thereof are also new and are therefore claimed as intermediate products in the synthesis of 7α, 17α-substituted 11β-halogen steroids with general formula 8 also according to the invention.

An especially preferred 7α-substituted 11β-haloestra-1,3,5(10)-triene with general formula 6 is 11β-fluoro-3-hydroxy-7α-methylestra-1,3,5(10)-trien-17-one.

The 7α, 17α-substituted 11β-halogen steroid with general formula 8 according to the invention can be formed from the 7α-substituted 11β-haloestra-1,3,5(10)-triene with general formula 6 in the same way as is previously described for the synthesis of the compound with general formula 10 by selective alkylation at $C^{17}$ of the ring skeleton.

In addition, 7α-substituted 11β-halogen steroids with general formula 9 can also be produced from the substances with general formula 4,B that are obtained by microbiological hydroxylation and oxidation from the 7α-substituted steroids with general formula 3,A or D, and said 7α-substituted 11β-halogen steroids also have androgenic action:

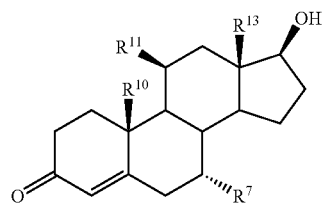

9 in which $R^7$, $R^{11}$ and $R^{13}$ have the same meanings as indicated above. An especially preferred compound is 11β-fluoro-17β-hydroxy-7α-methylestr-4-en-3-one. The compounds with general formula 9 as well as the pharmaceutically compatible addition salts, esters and amides thereof also have androgenic action.

For the production of compounds with general formula 9, estr-4-ene-3,17-dione 5 is reduced to 17β-hydroxy-estr-4-en-3-one 9, for example with a boron hydride.

In addition, the compounds with general formula 9 can be converted into the corresponding 7α-substituted 11β-haloestra-5(10)-enes:

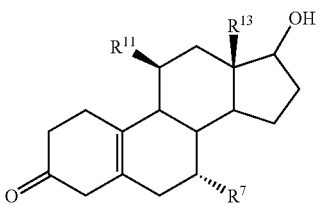

whereby $R^7$, $R^{10}$, $R^{11}$ and $R^{13}$ have the meanings as in general formulas 8, 10, and 12. For this purpose, the compounds with general formula 9 are isomerized by alteration of the $\Delta^4$-double bond into a $\Delta^{5(10)}$-double bond. To protect the 3-keto group, first a cyclic ether in 3-position is formed for this purpose. Then, the $\Delta^4$-double bond is isomerized into the $\Delta^{5(10)}$-double bond, whereby the above-indicated 7α-substituted 11β-halogen steroid is formed, and the protective group is then cleaved again.

Finally, the corresponding 7α-substituted 11β-haloestra-5(10)-enes can also be converted from the compounds with general formula 5 by isomerization of the $\Delta^4$-double bond into the $\Delta^{5(10)}$-double bond:

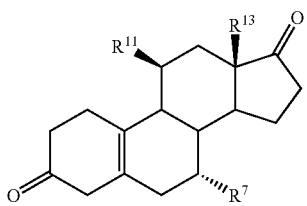

whereby $R^7$, $R^{10}$, $R^{11}$ and $R^{13}$ have the meanings as in general formulas 8, 10, and 12. For this purpose, the compounds with general formula 5 are isomerized by alteration of the $\Delta^4$-double bond into a $\Delta^{5(10)}$-double bond. To protect the 3-keto group, in turn first a cyclic ether is formed in 3-position for this purpose. Then, the $\Delta^4$-double bond is isomerized into the $\Delta^{5(10)}$-double bond, whereby the 7α-substituted 11β-halogen steroids that are indicated above are formed, and the protective group is finally cleaved again.

All above-mentioned compounds can also be further esterified or etherified if corresponding hydroxy groups are present in 3- or 17β-position. For example, compound 9 can be converted into a corresponding 17β-ether or 17β-ester. A preferred compound is 11β-fluoro-17β-(4-sulfamoylbenzoxy)-7α-methylestr-4-en-3-one. As substituents on the oxy-oxygen atom at $C^{17}$, basically the same radicals as are also indicated for $R^{17'}$ are suitable.

In particular, the 7α, 17α-substituted 11β-halogen steroids with general formulas 8, 10, and 12 are suitable for the production of pharmaceutical agents. This invention therefore also relates to the use of the above-mentioned compounds with general formulas 8, 10, and 12 for the production of pharmaceutical agents as well as pharmaceutical preparations that contain at least one of the above-mentioned compounds with general formulas 8, 10, and 12 as well as at least one pharmaceutically compatible vehicle.

The 7α, 17α-substituted 11β-halogen steroids with general formulas 10 and 12 are compounds with strong androgenic action without the above-mentioned side effects, for example stimulation of the prostate (especially no benign prostate hyperplasia). The compounds are easy to synthesize. It has been shown that the compounds according to the invention with general formula 10 or 12 can be used not only for male HRT, but these compounds, even without additional administration of other active ingredients, are also suitable as effective male contraceptive agents, if a sufficient metering is done to adequately reduce the blood level of LH, of testosterone that is produced in the body as well as of FSH (follicle-stimulating hormone). This depends on the 11β-halogen steroids according to the invention inhibiting the release of LH and FSH. LH stimulates the Leydig cells, so that testosterone is secreted. If the blood level of LH is kept low, the release of endogenous testosterone also drops. Testosterone is required for spermatogenesis, while FSH stimulates the germ cells. Sufficiently high FSH and LH blood levels are therefore necessary for an effective spermatogenesis, whereby a sufficiently high LH blood level results in the testosterone release that is necessary for spermatogenesis.

Since a treatment exclusively with the 7α, 17α-substituted 11β-halogen steroids can already result in effective male contraception without additional active ingredients for sterilization, the administration of a pharmaceutical agent that is suitable for this purpose can be significantly simplified, and the costs of use can be considerably lowered.

The 7α, 17α-substituted 11β-halogen steroids according to the invention can also be used in combination with a gestagen to control male fertility.

Moreover, the 7α, 17α-substituted 11β-halogen steroids according to the invention effectively inhibit 5α-reductase and the steroid-11-hydroxylase [CYP11B (P450c11), G. Zhang, W.L. Miller, *Journal of Clinical Endocrinology and Metabolism*, Vol. 81, pages 3254-3256 (1996)], such that, for example, the stimulation of the prostate is selectively avoided, and these compounds have an improved pharmacokinetics. The inhibition of the 11-hydroxylase results in a reduced deactivation of the androgenic compounds and in their reduced excretion from the human body. As a result, the effectiveness and the duration of action of these compounds compared to known compounds are improved especially after oral administration.

For the reasons above, these compounds are suitable especially for use in male birth control as well as for androgen replacement therapy with a reduced tendency toward 5α-reduction with simultaneously obtained aromatizability to form estrogenic steroids and an advantageous influence on serum lipids and the central nervous system.

The androgenic action and the observation that the above-mentioned side effects do not occur were determined with a seminal vesicle test for the compounds according to the invention with general formulas 10 and 12. The effectiveness of the compounds with general formula 8 according to the invention was checked for estrogenic action with a uterus growth test.

The 7α, 17α-substituted 11β-halogen steroids with general formula 10 or 12 according to the invention or the pharmaceutical preparations according to the invention that contain these compounds are extremely well suited for treating non-sterile male patients as well as basically also male mammals. An application for male contraception results in that the male patients are only temporarily sterile. After the application of the active ingredients according to the invention or the pharmaceutical preparations is completed, the original state is produced again, so that the male patient is no longer sterile, and the spermatogenesis takes place again to the original extent. To keep the condition of temporary sterility constant over a desired period, the administration of the active ingredient or the preparation is to be performed continuously, whereby the administration, depending on the form of administration, is to be repeated daily, at a shorter interval or else periodically at a longer interval. After the one-time or repeated administration of the active ingredient or the preparation is completed, the non-sterile condition of the male patient optionally is not immediately restored but rather only slowly restored, whereby the time span that is necessary for this purpose depends on various factors, for example the dosage, the body constitution of the patients and the parallel administration of other pharmaceutical agents.

If the purpose of administration consists in contraception, the dosage of the 7α, 17α-substituted 11β-halogen steroids must be set high such that the blood levels of LH and FSH in each case are at most 2.5 I.E./ml (I.E.: International Units), especially at most 1.0 I.E./ml, and the blood level of testosterone is at most 10 nmol/l, especially at most 3 nmol/l.

If the 7α, 17α-substituted 11β-halogen steroids according to the invention are to be used for HRT without a contraception being achieved, the dosage is set lower. For this case, an attempt is made to achieve effect levels that make possible the blood levels for LH and FSH of respectively more than 2.5 I.E./ml and for testosterone of more than 10 nmol/l.

The dosages of the 7α, 17α-substituted 11β-halogen steroids with general formula 10 or 12 according to the invention that are required to set the blood level of LH, FSH and testosterone depend on a number of factors and must therefore be determined in an administration-specific manner. First, the dosage is naturally dependent on the type of therapy. If the compounds are to be used for male contraception, significantly higher doses must be given than in the case of a use for HRT. The dosage also depends on the type of 7α, 17α-substituted 11β-halogen steroid and its bio-availability. The type of administration is also essential for the amount to be administered. Finally, the dosage also depends on the body constitution of the patient to be treated and other factors, for example the state of whether other pharmaceutical agents are provided in parallel.

The compounds can be administered orally and parenterally, for example i.p. (intraperitoneally), i.v. (intravenously), i.m. (intramuscularly) or percutaneously. The compounds can also be implanted in the tissue. The amount of the compounds to be administered can fluctuate within a wide range if an effective amount is administered. Based on the condition to be treated and the type of dispensing, the amount of administered compound can vary within a wide range. In humans, the daily dose is in the range of 0.1 to 100 mg. The preferred daily dosage in humans is 0.1 to 10 mg. The duration of administration depends on the purpose to be achieved.

Capsules, pills, tablets, coated tablets, creams, ointments, lotions, liquids, such as syrups, gels, injectable liquids, for example for i.p., i.v., i.m. or percutaneous injection, etc., are suitable for use, whereby the individual forms for dispensing release the compounds according to the invention to the body gradually or in the entire amount within a short time depending on the type thereof.

For oral administration, capsules, pills, tablets, coated tablets and liquids or other known oral forms for dispensing are used as pharmaceutical preparations. In this case, the pharmaceutical agents can be formulated in such a way that they release the active ingredients either in a short time and deliver them to the body or they have a depot action, so that a prolonged, slow feed of active ingredient to the body is achieved. In addition to the 7α, 17α-substituted 11β-halogen steroid, the dosage units can contain one or more pharmaceutically compatible vehicles, for example substances for adjusting the rheology of the pharmaceutical agent, surfactants, solubilizers, microcapsules, microparticles, granulates, diluents, binders, such as starch, sugar, sorbitol and gelatin, also fillers, such as silicic acid and talc, lubricants, dyes, perfumes and other substances.

In particular, the 7α, 17α-substituted 11β-halogen steroids according to the invention can also be formulated in the form of a solution that is intended for oral administration and that in addition to the active 11β-halogen steroid contains as the following components: a pharmaceutically compatible oil and/or a pharmaceutically compatible lipophilic surfactant and/or a pharmaceutically compatible hydrophilic surfactant and/or a pharmaceutically compatible water-miscible solvent. In this respect, reference is also made to WO-A-97/21440.

To achieve better bio-availability of the steroid, the compounds can also be formulated as cyclodextrin clathrates. For this purpose, the compounds are reacted with α-, β- or γ-cyclodextrin or derivatives thereof.

If creams, ointments, lotions and liquids that can be applied topically are to be used, the latter must be constituted in such a way that the compounds according to the invention are fed to the body in a sufficient amount. In these forms for dispensing, adjuvants are contained, for example substances for adjusting the rheology of pharmaceutical agents, surfactants, preservatives, solubilizers, diluents, substances for increasing the permeability of the steroids according to the invention through the skin, dyes, perfumes and skin protection agents, such as conditioners and moisturizers. Together with the steroids according to the invention, other active ingredients can also be contained in the pharmaceutical agent.

For parenteral administration, the active ingredients can be dissolved or suspended in a physiologically compatible diluent. As diluents, very often oils with or without the addition of a solubilizer, a surfactant, a suspending agent or emulsifier are used. Examples of oils that are used are olive oil, peanut oil, cottonseed oil, soybean oil, castor oil and sesame oil. To formulate an injectable preparation, any liquid vehicle can be used in which the compounds according to the invention are dissolved or emulsified. These liquids frequently also contain substances to regulate viscosity, surfactants, preservatives, solubilizers, diluents and other additives, with which the solution is set to isotonic. Other active ingredients can also be administered together with the 7α, 17α-substituted 11β-halogen steroids.

The 11β-halogen steroids according to the invention can be administered in the form of a depot injection or an implant preparation, for example subcutaneously, which can be formulated in such a way that a delayed release of active ingredients is made possible. To this end, known techniques can be used, for example depots that dissolve or that operate with a membrane. Implants can contain as inert materials, for example, biodegradable polymers or synthetic silicones, for example silicone gum. The 11β-halogen steroids according to the invention can also be incorporated in, for example, a patch, for percutaneous administration.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The examples that are indicated below are used for a more detailed explanation of the invention:

A. Microbiological Synthesis:

11α-Hydroxy-7α-methyl-estr-4-ene-3,17-dione (Compound 4,B)

EXAMPLE 1:

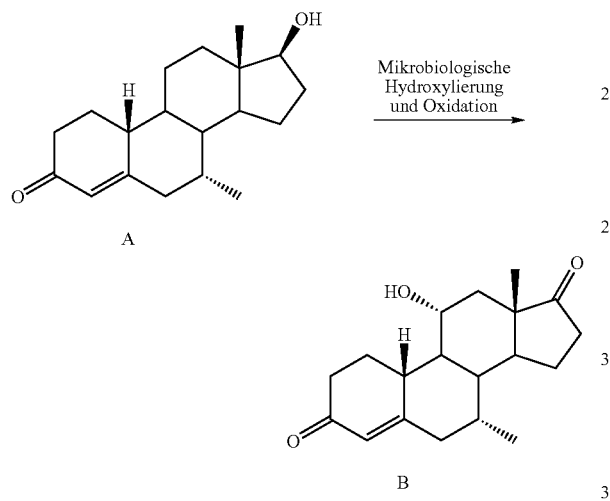

[Key: Mikrobiologische Hydroxylierung und Oxidation = Microbiological Hydroxylation and Oxidation]

A 2 l Erlenmeyer flask that contained 1000 ml of a nutrient solution, sterilized for 30 minutes at 121° C. in an autoclave, that consists of 3% by weight of glucose, 1% by weight of corn steep liquor, 0.2% by weight of NaNO$_3$, 0.1% by weight of KH$_2$PO$_4$, 0.2% by weight of K$_2$HPO$_4$, 0.05% by weight of KCl, 0.05% by weight of MgSO$_4$7H$_2$O and 0.002% by weight of FeSO$_4$7H$_2$O (pH 6.0) was inoculated with a slant rod culture of the strain *Gnomonia cingulata* (CBS 15226) and shaken for 72 hours at 28° C. in a rotary shaker at 165 rpm. With this preculture, a 20 l fermenter that was coated with 19 l of sterile medium of the same final composition as described for the preculture was inoculated. In addition, before the sterilization, another 1.0 ml of silicone oil and 1.0 ml of synperonic (oxoalcohol ethoxylate) were added for foam abatement. After a growth phase of 12 hours at 0.7 bar of overpressure, a temperature of 28° C., an aeration of 20 l/minute and a stirring speed of 250 rpm, a solution of 4.0 g of 17β-hydroxy-7α-methylestr-4-en-3-one in 40 ml DMF was added. Stirring was continued, and it was aerated. After 135 hours, the culture broth was harvested and extracted for 12 hours with 10 l of methyl isobutyl ketone and for 5 hours with 5 l of methyl isobutyl ketone. The combined organic phases were evaporated to the dry state. The silicone oil was washed out with hexane. After chromatography on silica gel with a gradient that consists of hexane and ethyl acetate, 1.64 g (39%) of 11α-hydroxy-17α-methylestr-4-ene-3,17-dione was isolated.

EXAMPLE 2:

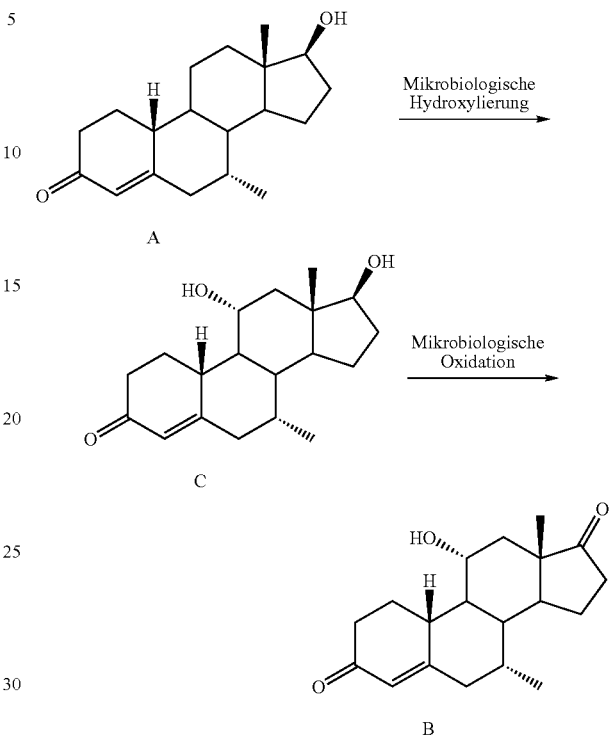

[Key: Mikrobiologische Hydroxylierung = Microbiological Hydroxylation
Mikrobiologische Oxidation = Microbiological Oxidation]

A 2 l Erlenmeyer flask that contained 1000 ml of a nutrient solution, sterilized for 30 minutes at 121° C. in an autoclave and consisting of 3% by weight of glucose, 1% by weight of corn steep liquor, 0.2% by weight of NaNO$_3$, 0.1% by weight of KH$_2$PO$_4$, 0.2% by weight of K$_2$HPO$_4$, 0.05% by weight of KCl, 0.05% by weight of MgSO$_4$7H$_2$O, and 0.002% by weight of FeSO$_4$7H$_2$O (pH 6,0), was inoculated with a slant rod culture of the strain *Glomerella cingulata* (IFO 6425) and shaken for 72 hours at 28° C. in a rotary shaker at 165 rpm. With this preculture, a 20 l fermenter was inoculated, and said fermenter was coated with 19 l of a sterile medium of the same final composition as described for the preculture. In addition, before the sterilization, another 1.0 ml of silicone oil and 1.0 ml of synperonic were added for foam abatement. After a growth phase of 12 hours at 0.7 bar of overpressure, a temperature of 28° C., an aeration of 10 l/minute and a stirring speed of 350 rpm, a solution of 2.0 g of 17β-hydroxy-7α-methylestr-4-en-3-one in 30 ml DMF was added. Stirring was continued, and it was aerated. After 19 hours, the culture broth was harvested and extracted for 16 hours with 20 l of methyl isobutyl ketone and for 23 hours with 20 l of methyl isobutyl ketone. The combined organic phases were evaporated to the dry state. The residue was dissolved to a large extent in methanol. The silicone oil was filtered off. It was concentrated by evaporation, and after chromatography on silica gel with a gradient that consists of dichloromethane and acetone, 1.55 g (73%) of 11α, 17β-dihydroxy-7α-methylestr-4-en-3-one was isolated. After recrystallization from acetone/diisopropyl ether, 827 mg (39%) of white crystals with a melting point of 163° C. and $[α]_D = -16°$ (CHCl$_3$, c=0.501) was isolated.

A 2 l Erlenmeyer flask that contained 500 ml of a nutrient solution, sterilized for 30 minutes at 121° C. in an autoclave and consisting of 0.5% by weight of glucose, 0.5% by weight of bacto-yeast extract, 0.1% by weight of peptone, and 0.2% by weight or corn steep liquor (pH 7.5), was inoculated with four cryospheres from a culture of the strain Bacillus sphaericus (ATCC 7055) and shaken for 24 hours at 28° C. in a rotary shaker at 165 rpm. With this preculture, four 2 l Erlenmeyer flasks that contained 500 ml of sterile medium of the same composition as described for the preculture were inoculated with 10% each of this culture broth. After a growth phase of 4 hours at a temperature of 28° C. in a rotary shaker at 165 rpm, a solution of 50 mg of 11α, 17β-dihydroxy-7α-methylestr-4-en-3-one in 2.5 ml DMF was added to each flask. Shaking was continued for 48 hours. The combined culture broths were extracted twice with 2 l of methyl isobutyl ketone. The combined organic phases were dried on sodium sulfate and evaporated to the dry state. In this case, 630 mg of an oily-crystalline residue was obtained. After recrystallization from acetone/diisopropyl ether, 103 mg (49.2%) of yellowish crystals with a melting point of 189° C. and $[\alpha]_D=+40.4°$ (CHCl$_3$, c=0.529) was isolated (direct crystallization without previous chromatographic purification).

EXAMPLE 3:

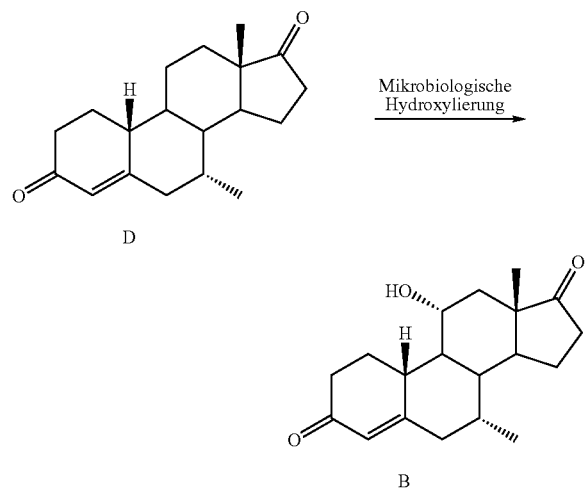

[Key: Mikrobiologische Hydroxylierung = Microbiological Hydroxylation]

A 2 l Erlenmeyer flask that contained 500 ml of a nutrient solution, sterilized for 30 minutes at 121° C. in an autoclave and consisting of 3% by weight of glucose, 1% by weight of corn steep liquor, 0.2% by weight of NaNO$_3$, 0.1% by weight of KH$_2$PO$_4$, 0.2% by weight of K$_2$HPO$_4$, 0.05% by weight of KCl, 0.05% by weight of MgSO$_4$7H$_2$O, and 0.002% by weight of FeSO$_4$7H$_2$O (pH 6.0), was inoculated with a half slant rod culture of the strain Aspergillus ochraceus (CBS 13252) and shaken for 72 hours at 28° C. in a rotary shaker at 165 rpm. With this preculture, a 10 l fermenter was inoculated, and said fermenter was coated with 9.5 l of a sterile medium of the same final composition as described for the preculture. In addition, before the sterilization, another 0.5 ml of silicone oil and 0.5 ml of synperonic were added for foam abatement. After a growth phase of 6 hours at 0.7 bar of overpressure, a temperature of 28° C., an aeration of 5 l/minute and a stirring speed of 350 rpm, a solution of 1.0 g of 7α-methylestr-4-ene-3,17-dione in 15 ml DMF was added. Stirring was continued, and it was aerated. After 22 hours, the culture broth was harvested and extracted twice for 4 hours with 7 l of methyl isobutyl ketone. The combined organic phases were evaporated to the dry state. The residue was dissolved to a large extent in methanol. The silicone oil was filtered off. It was concentrated by evaporation, and after chromatography on silica gel with a gradient that consists of dichloromethane and acetone, 0.78 g (74%) of 11α-hydroxy-7α-methylestr-4-ene-3,17-dione was isolated. After recrystallization from acetone/diisopropyl ether, 311 mg (29.6%) of white crystals with a melting point of 200° C. and $[\alpha]_D=+52°$ (CHCl$_3$, c=0.5905) was isolated.

B. Chemical Production Process:

EXAMPLE 4

Production of 11β-fluoro-17β-hydroxy-7α-methyl-estr-4-en-3-one:

a) 11β-Fluoro-7α-methyl-estr-4-ene-3,17-dione:

11.5 ml of perfluorobutane-1-sulfonic acid fluoride was added in drops at 0° C. to a solution of 13.08 g of 11α-hydroxy-7α-methyl-estr-4-ene-3,17-dione (produced by means of microbiological synthesis according to the invention [Part A]) in 250 ml of toluene and 18.2 ml of 1,8-diazabicyclo[5,4,0]undec-7-ene. After 1 hour, it was neutralized with 2 M hydrochloric acid, added to water, extracted four times with ethyl acetate, washed with saturated sodium chloride solution, dried and concentrated by evaporation in a vacuum. After the crude product was chromatographed on silica gel with a hexane/ethyl acetate gradient, 8.7 g of 11β-fluoro-7α-methyl-estr-4-ene-3,17-dione was obtained. Melting point: 101.4° C., $[\alpha]_D$: +135.8° (CHCl$_3$).

b) 11β-Fluoro-17β-hydroxy-7α-methylestr-4-en-3-one:

A solution of 8.7 g of 11β-fluoro-7α-methyl-estr-4-ene-3,17-dione in 148 ml of tetrahydrofuran was mixed drop by drop at 0° C. with 29.5 ml of 1 M lithium aluminium tri-tert-butoxyhydride in tetrahydrofuran and stirred for 5.5 hours at 0° C. Then, dilute sulfuric acid was added at 0° C., and the reaction solution was added to ice water, extracted three times with ethyl acetate, washed neutral, dried on sodium sulfate, concentrated by evaporation in a vacuum and chromatographed on silica gel with hexane/ethyl acetate. 5.8 g 11β-fluoro-17β-hydroxy-7α-methylestr-4-en-3-one with a melting point of 143-144° C. was obtained. $[\alpha]_D=+89.9°$ (CHCl$_3$).

EXAMPLE 5

Production of 11β-Fluoro-17β-(4-sulfamoylbenzoxy)-7α-methylestr-4-en-3-one:

A solution of 500 mg of 11β-fluoro-17β-hydroxy-7α-methylestr-4-en-3-one in 7.5 ml of pyridine was mixed at room temperature with 750 mg of 4-sulfamoylbenzoic acid, 800 mg of N,N-dicyclohexylcarbodiimide as well as 125 mg of p-toluenesulfonic acid and stirred for 8.5 hours. Then, it was added to sodium bicarbonate solution, extracted four times with dichloromethane, washed neutral, dried on sodium sulfate, concentrated by evaporation in a vacuum, and chromatographed on silica gel with dichloromethane/acetone. 302 mg of 11β-fluoro-17β-(4-sulfamoylbenzoxy)-

7α-methylestr-4-en-3-one with a melting point of 232° C. was obtained. $[\alpha]_D=+100.5°$ (CHCl$_3$).

EXAMPLE 6

Production of 17α-Ethinyl-11β-fluoro-17β-hydroxy-7α-methylestr-4-en-3-one:

a) 11β-Fluoro-3-methoxy-7α-methylestra-3,5-dien-17-one:

A solution of 2 g of 11β-fluoro-7α-methylestr-4-ene-3,17-dione in 20 ml 2,2-di-methoxypropane was stirred with 200 mg of pyridinium tosylate for 6.5 hours at 80° C. Then, it was diluted with ethyl acetate, washed with sodium bicarbonate solution and sodium chloride solution, dried on sodium sulfate and concentrated by evaporation in a vacuum. 2 g of crude 11β-fluoro-3-methoxy-7α-methylestra-3,5-dien-17-one was obtained.

b) 17α-Ethinyl-11β-fluoro-17β-hydroxy-7α-methylestr-4-en-3-one

A solution of 9.17 g of cerium(III) chloride in 60 ml of tetrahydrofuran was mixed drop by drop at 0° C. with 74.2 ml of an ethinylmagnesium bromide solution (0.5 M in tetrahydrofuran) and stirred for 1 hour at 0° C. Then, a solution of 2 g of crude 11β-fluoro-3-methoxy-7α-methylestra-3,5-dien-17-one in 40 ml of tetrahydrofuran was added drop by drop and stirred for another 3.5 hours at 0° C. For working-up, a saturated ammonium chloride solution was added, added to water, extracted three times with ethyl acetate, washed with semiconcentrated hydrochloric acid, sodium bicarbonate solution and sodium chloride solution, dried on sodium sulfate, concentrated by evaporation in a vacuum and chromatographed on silica gel with hexane/ethyl acetate. 1.15 g of pure 17α-ethinyl-11β-fluoro-17β-hydroxy-7α-methylestr-4-en-3-one with a melting point of 218-220° C. was obtained. $[\alpha]_D=+19.2°$ (CHCl$_3$).

EXAMPLE 7

Production of 17α-Ethinyl-11β-fluoro-17β-hydroxy-7α-methylestr-5(10)-en-3-one:

a) 3,3-Ethanediyldioxy-17α-ethinyl-11β-fluoro-7α-methylestr-5(10)-en-17β-ol:

A solution of 700 mg of 17α-ethinyl-11β-fluoro-17β-hydroxy-7α-methylestr-4-en-3-one in 7 ml dichloromethane and 4.7 ml of ethylene glycol was stirred with 2.3 ml of trimethyl orthoformate and 30 mg of p-toluenesulfonic acid hydrate for 6.5 hours at room temperature. Then, it was added to sodium bicarbonate solution, extracted three times with ethyl acetate, washed neutral, dried on sodium sulfate, concentrated by evaporation in a vacuum, and chromatographed on silica gel with hexane/ethyl acetate. 205 mg of 3,3-ethanediyldioxy-17α-ethinyl-11β-fluoro-7α-methylestr-5(10)-en-17β-ol was obtained.

b) 17α-Ethinyl-11β-fluoro-17β-hydroxy-7α-methylestr-5(10)-en-3-one:

A solution of 205 mg of 3,3-ethanediyldioxy-17α-ethinyl-11β-fluoro-7α-methylestr-5(10)-en-17β-ol in 27 ml of methanol and 3.6 ml of water was stirred with 361 mg of oxalic acid for 24 hours at room temperature. Then, it was added to sodium bicarbonate solution, extracted three times with ethyl acetate, washed neutral, dried on sodium sulfate, concentrated by evaporation in a vacuum and chromatographed on silica gel with hexane/ethyl acetate. 95 mg of 17α-ethinyl-11β-fluoro-17β-hydroxy-7α-methylestr-5(10)-en-3-one with a melting point of 112-114° C. was obtained.

EXAMPLE 8

Production of 17α-Ethinyl-11β-fluoro-7α-methyl-estra-1,3,5(10)-triene-3,17β-diol:

a) 11β-Fluoro-3-hydroxy-7α-methylestra-1,3,5(10)-trien-17-one:

A solution of 500 mg of 11β-fluoro-7α-methylestr-4-ene-3,17-dione in 16.5 ml of acetonitrile was stirred with 400 mg of copper(II) bromide for 6.5 hours at 25° C. Then, it was diluted with ethyl acetate, washed with sodium bicarbonate solution and sodium chloride solution, dried on sodium sulfate, concentrated by evaporation in a vacuum and chromatographed on silica gel with hexane/acetone. 280 mg of pure 11β-fluoro-3-hydroxy-7α-methylestra-1,3,5(10)-trien-17-one with a melting point of 185-186° C. was obtained.

b) 17α-Ethinyl-11β-fluoro-7α-methylestra-1,3,5(10)-triene-3,17β-diol:

A suspension of 2.03 g of cerium(III) chloride in 7.5 ml of tetrahydrofuran was mixed drop by drop at 0° C. with 16.5 ml of an ethinylmagnesium bromide solution (0.5 M in tetrahydrofuran) and stirred for 0.5 hour at 0° C. Then, a solution of 280 mg of 11β-fluoro-3-hydroxy-7α-methyl-estra-1,3,5(10)-trien-17-one in 2.8 ml tetrahydrofuran was added drop by drop and stirred for another 3.5 hours at 0° C. For working-up, a saturated ammonium chloride solution was added, added to water, extracted four times with ethyl acetate, washed neutral, dried on sodium sulfate, concentrated by evaporation in a vacuum and chromatographed on silica gel with hexane/ethyl acetate.

220 mg of 17α-ethinyl-11β-fluoro-7α-methylestra-1,3,5(10)-triene-3,17β-diol with a melting point of 115-117° C. was obtained.

The entire disclosures of all applications, patents and publications, cited herein and of corresponding German application No. 10233723.3, filed Jul. 24, 2002, and U.S. Provisional Application Ser. No. 60/402,953, filed Aug. 14, 2002, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A microbiological process for the production of a 7α-substituted 11α-hydroxy steroids of formula 4,B

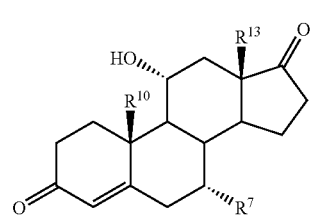

wherein
R⁷ is P—Q, wherein P is a $C_1$- to $C_4$-alkylene, and Q is hydrogen, $C_1$- to $C_4$-alkyl- or $C_1$- to $C_4$-fluoroalkyl, and wherein P—Q is bonded via P to the steroid skeleton,
R¹⁰ is either in α- or β-position and is H, $CH_3$ or $CF_3$, and
R¹³ is methyl or ethyl,
comprising hydroxylating and oxidizing of a 7α-substituted steroid of formula 3,A,

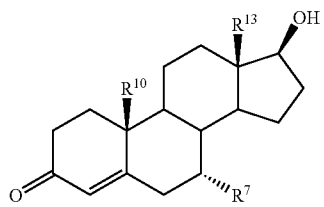

3, A wherein R⁷, R¹⁰ and R¹³ are as indicated above, with use of a microorganism which is *Aspergillus* sp., *Beauveria* sp., *Glomerella* sp., *Gnomonia* sp., *Haplosporella* sp. or *Rhizopus* sp.

2. A process according to claim 1, wherein the microorganism is *Aspergillus awamori*, *Aspergillus fischeri*, *Aspergillus malignus*, *Aspergillus niger*, *Beauveria bassiana*, *Glomerella cingulata*, *Gnomonia cingulata*, *Haplosporella hesperedica* or *Rhizopus stolonifer*.

3. A microbiolociical process for the production of 7α-substituted 11 α-hydroxy steroid of formula 4,B

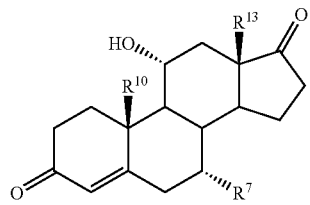

4, B wherein
R⁷ is P—Q, wherein P is a $C_1$- to $C_4$-alkylene and Q is hydrogen, a $C_1$- to $C_4$-alkyl- or $C_1$- to $C_4$-fluoroalkyl, and wherein P—Q is bonded via P to the steroid skeleton,
R¹⁰ is either in α- or β-position and is H, $CH_3$ or $CF_3$, and
R¹³ is methyl or ethyl,
comprising hydroxylating of a 7α-substituted steroid of formula 3,A in 11α-position,

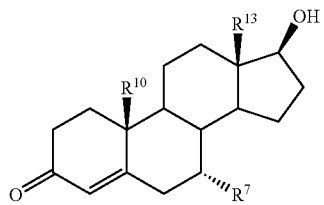

3, A wherein R⁷, R¹⁰ and R¹³ are as previously indicated, using a first microorganism which is *Aspergillus* sp., *Beauveria* sp., *Gibberella* sp., *Glomerella* sp., *Gnomonia* sp., *Metarrhizium* sp., *Nigrospora* sp., *Rhizopus* sp. or *Verticillium* sp., to form a 7α-substituted 11α-hydroxy steroid of formula C:

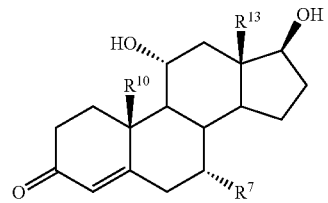

C wherein R⁷, R¹⁰ and R¹³ are as indicated above, and oxidizing the 7α-substituted 11α-hydroxy steroid product of formula C with use of a second microorganism which is *Bacillus* sp., *Mycobacterium* sp., *Nocardia* sp. or *Pseudomonas* sp.

4. A process according to claim 3, wherein the first microorganism is *Aspergillus malignus*, *Aspergillus melleus*, *Aspergillus niger*, *Aspergillus ochraceus*, *Beauveria bassiana*, *Gibberella fujikuroi*, *Gibberella zeae*, *Glomerella cingulata*, *Glomerella fusaroides*, *Gnomonia cingulata*, *Metarrhizium anisopliae*, *Nigrospora sphaerica*, *Rhizopus oryzae*, *Rhizopus stolonifer* or *Verticillium dahliae*.

5. A process according to claim 3, wherein the second microorganism is *Bacillus lactimorbus*, *Bacillus sphaericus*, *Mycobacterium neoaurum*, *Mycobacterium smegmatis*, *Nocardia corallina*, *Nocardia globerula*, *Nocardia minima*, *Nocardia restrictus*, *Nocardia rubropertincta*, *Nocardia salmonicolor* or *Pseudomonas testosteroni*.

6. A microbiological process for the production of a 7α-substituted 11α-hydroxy steroids of formula 4,B

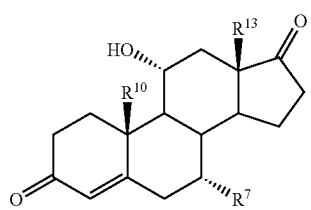

4, B wherein
R⁷ is P—Q, wherein P is a $C_1$- to $C_4$-alkylene, and Q is hydrogen, $C_1$- to $C_4$-alkyl- or $C_1$- to $C_4$-fluoroalkyl, and wherein P—Q is bonded via P to the steroid skeleton,
R¹⁰ is either in α- or β-position and is H, $CH_3$ or $CF_3$, and
R¹³ is methyl or ethyl,
comprising hydroxylating 7α-substituted steroids of formula D:

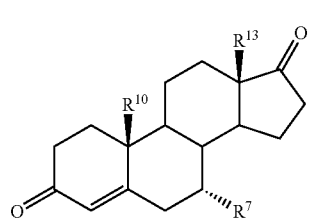

D wherein $R^7$, $R^{10}$ and $R^{13}$ are as indicated above, using a microorganism which is *Beauveria* sp., *Curvularia* sp., *Gibberella* sp., *Glomerella* sp., *Gnomonia* sp., *Haplosporella* sp., *Helicostylum* sp., *Nigrospora* sp., or *Syncephalastrum* sp.

7. A process according to claim 6, wherein the microorganism is *Beauveria bassiana, Curvularia lunata, Gibberella zeae, Glomerella cingulata, Glomerella fusaroides, Gnomonia cingulata, Haplosporella hesperedica, Helicostylum piriformae, Nigrospora sphaerica*, or *Syncephalastrum racemosum*.

8. A microbiological process according to claim 1, wherein $R^7$ stands for $CH_3$.

9. A microbiological process according to claim 1, wherein $R^{10}$ stands for H.

10. A microbiological process according to claim 1, wherein $R^{13}$ stands for $CH_3$.

* * * * *